US00PP16254P3

(12) United States Plant Patent
Glenn

(10) Patent No.: US PP16,254 P3
(45) Date of Patent: Feb. 14, 2006

(54) OAK TREE NAMED 'QNSTD'

(50) Latin Name: *Quercus nuttallii*
Varietal Denomination: QNSTD

(75) Inventor: Michael M. Glenn, Bogart, GA (US)

(73) Assignee: Tree Introductions, Inc., Bishop, GA (US)

( * ) Notice: Subject to any disclaimer, the term of this patent is extended or adjusted under 35 U.S.C. 154(b) by 77 days.

(21) Appl. No.: 10/850,689

(22) Filed: May 21, 2004

(65) Prior Publication Data

US 2005/0262603 P1 Nov. 24, 2005

(51) Int. Cl.
*A01H 5/00* (2006.01)

(52) U.S. Cl. ..... Plt./225

(58) Field of Classification Search ..... Plt./225
See application file for complete search history.

*Primary Examiner*—Anne Marie Grunberg
*Assistant Examiner*—Annette H Para
(74) *Attorney, Agent, or Firm*—Klarquist Sparkman, LLP

(57) ABSTRACT

An oak tree named 'QNSTD' having a dense branching habit and consistent red new growth persisting in summer, and also capable of being reproduced reliably using vegetative cuttings.

7 Drawing Sheets

Latin name of genus and species: *Quercus nuttallii.*
Variety denomination: 'QNSTD'.

BACKGROUND OF THE INVENTION

The present invention relates to a new and distinct variety of *Quercus nuttallii,* which has been given the varietal name 'QNSTD'. I discovered my new tree in 2000 as a chance seedling in a cultivated area of a nursery in Oconee County, Ga.

The parentage of this tree is unclear. It is definitely a red oak type tree. Representative species include Pin Oak (*Q. palustris*), or Red Oak (*Q. rubra*). There are also several related species, including Nuttal Oak (*Q. nuttallii*), Shumard Oak (*Q. shumardii*), and Scarlet Oak (*Q. coccinea*). My new tree has characteristics and a history that have prevented making an exact identification of its species, but Nuttall Oak appears to be the closest.

Nuttall Oak, as well as most other red oak types, readily hybridize with one another, and there is a high probability that this tree is a result of a cross between a Nuttall Oak and Shumard Oak or some other species of red oak, since Nuttall Oak and Shumard Oak overlap one another across much of their range. For example, in Texas, Nuttall is found in the lower Southeast corner of the state, Shumard is located in a wide band covering most of the eastern part of the state, and Texas Red Oak (*Q. texana*), is the primary tree in the central part of the state east of Dallas. There is also a large swath of habitat between the primary Shumard and Texas Red Oak regions where the predominant tree is a hybrid between Shumard and Texas Road Oak. Hybrids are common and can easily make up a large population of the trees in any given area.

My original tree had been purchased as a 12 to 18 inch liner in spring 1998 and at that time planted in a liner field. This tree was transplanted to another field in spring 2000 and was subsequently discovered by me. In December 2003, it was transplanted to an observation area where it has remained since that time. It is now 7 years old from a seed. The description of this new Oak variety is based on observations of this original tree and of up to three year old asexually propagated progeny, produced from vegetative propagation that are being grown at a nursery in Oconee County, Ga.

The original tree has displayed characteristics resembling Nuttal Oak and Shumard Oak. There is much confusion over the exact identification of this tree, and several experienced individuals have expressed differing options. The only consistency has been the opinion that the acorn is generally the most distinguishing characteristic determining the species difference between Nutall Oak and Shumard Oak. When compared to the above oaks, the acorns on my new tree most resemble Nuttall Oak, which indicates that the tree is most likely a Nuttall Oak or at least has Nuttall Oak as one of its parents. Other physical characteristics of the tree, such as leaf size, sinus depth, or bud features, do not provide definitive answers as to the true parentage of the tree.

BRIEF SUMMARY OF THE INVENTION

The original tree of my new variety was discovered in a cultivated area containing other Nuttal oaks (*Quercus nuttallii*) produced from seed. As I observed the original tree of my new variety, the uniqueness of this tree became apparent because of its dense branching habit, its distinct deep red new foliage color when the leaves emerge in the spring, and consistent red new growth persisting into summer. This red color remains until June in Oconee County, Ga. This deep red new foliage color when leaves emerge in the spring is the primary difference between my new tree and other *Quercus nuttallii* cultivars. These characteristics distinguish my new tree from other Nuttall Oaks of which I am aware.

My new variety has been asexually propagated by softwood cuttings in 2001 at my direction in Oconee County, Ga. The progeny have thus far proven to retain the dense branching habit and consistent red new growth persisting into summer of the original tree, even as smaller plants. This propagation and observation of the resulting progeny demonstrates that the 'QNSTD' variety reproduces true to type in successive generations of asexual reproduction. Furthermore, these observations have confirmed that my new variety represents a new and improved variety of oak tree, which appears to be a variation of Nuttall Oak trees based upon observations of acorns in the original tree and as particularly evidenced by the dense branching pattern and consistent red new growth persisting in summer, and which can reliably be asexually propagated using vegetative propagation.

I observed this tree of my new variety for a period of time and believe it is particularly useful as a specimen or for groupings in lawns, parks, golf courses, commercial landscapes, and a street tree. It provides good shade, has an above average growing rate, and has good structural branching. It also provides ornamental interest with its consistent red new growth persisting in summer.

Cultivated Nuttall Oak is represented in the industry mostly by seedling material. Seedling material has a wide range of variability, and as is illustrated by information in this patent, there may be uncertainty as to the trueness of type from the seed. My new tree has a dense branching habit and consistent red new growth persisting in summer not represented consistently by any other Nuttall Oak tree cultivar known to me. 'QNFTA' (U.S. Plant Pat. No. 13,524) and 'QNSTC' (U.S. patent application Ser. No. 10/823,472) are Nuttall cultivars that have an upright-pyramidal branching habit, and a consistent red fall colored foliage. However, both of these selections lack a consistent red new growth persisting into summer.

Typical Nutall and Shumard are pyramidal trees that become more spreading with age. 'QNSTD' has a dense shape and a full, dense canopy and a central leader that is more typical of a Nuttall Oak tree. Both Nuttall Oak and Shumard Oak typically reach 40 to 60 feet high and wide in the landscape, but can reach 100 feet or more in nature. The ultimate height and width of 'QNSTD' is not known.

BRIEF DESCRIPTION OF THE DRAWINGS

The accompanying photographs depict the color of the tree and foliage of my new variety as nearly as is reasonably possible to make the same in a color illustration of this character.

DETAILED BOTANICAL DESCRIPTION

My 'QNSTD' variety of Oak tree is currently growing at an observation site in Oconee County, Ga. It is located in an area of Oconee that has a clay loam soil type and receives approximately 50 inches of rain per year. Oconee County, Ga. is in USDA Hardiness Zone 7. Both Nutall and Shumard are typically hardy in USDA Zones 5 through 9.

My new tree has not been observed under all growing conditions, and thus, variations may occur as a result of different growing conditions. The following is a detailed description of my new variety of my new tree with color terminology in accordance with The Royal Horticultural Society (R.H.S.) Colour chart published by The Royal Horticultural Society in London. The observations are of the original seven year old tree growing at the observation site in Oconee County, Ga. and, where young trees are indicated below, the observations are of up to three year old progeny growing at this location.

Parentage: Discovered as a chance seedling in a production field at a nursery in Oconee County, Ga. The parentage of this tree is believed to include Nuttall Oak, but is not extremely clear for reasons explained above.

Figure 1:
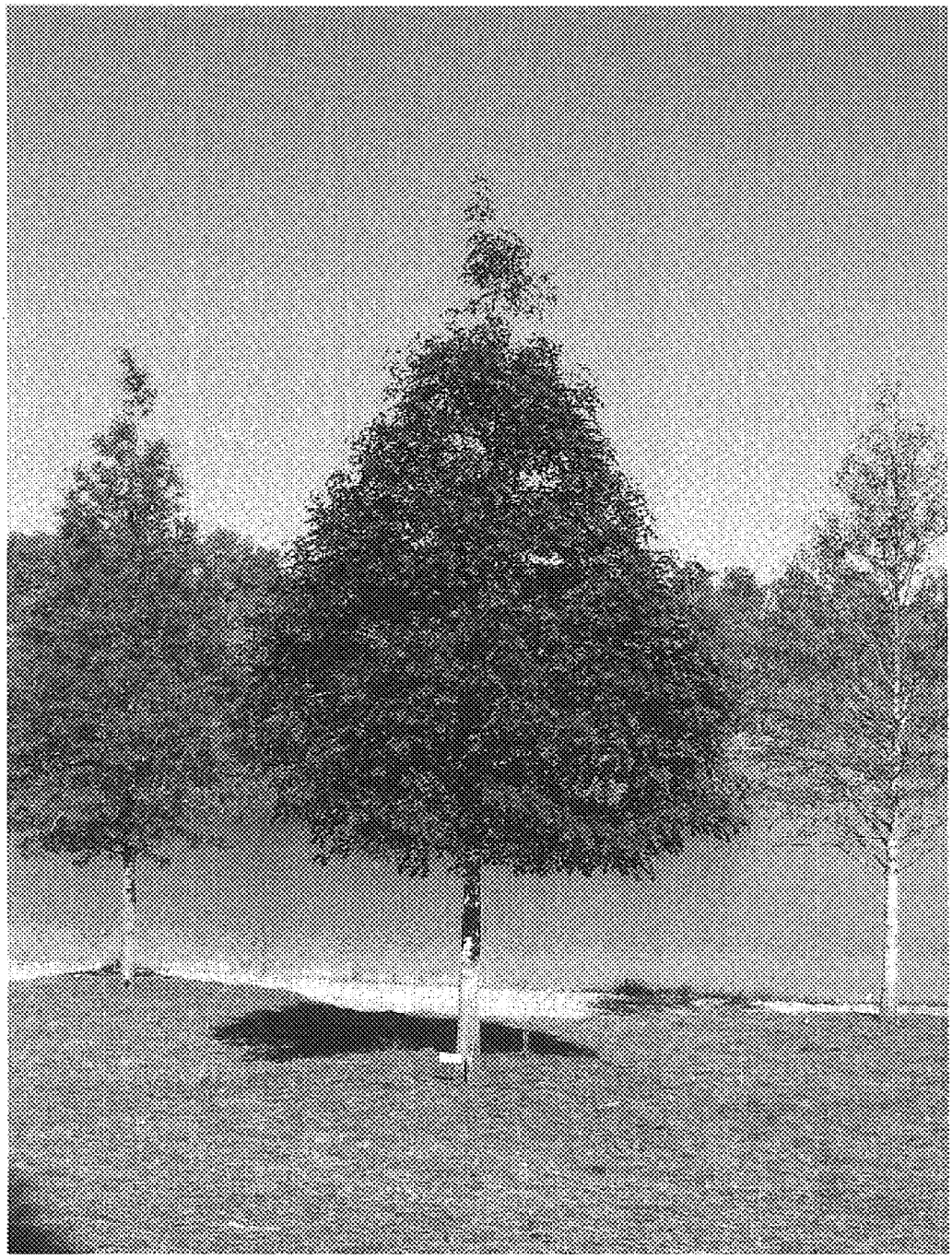
FIG. 1 is a photograph of the original tree of my new variety during the spring with red new growth.
Figure 2:
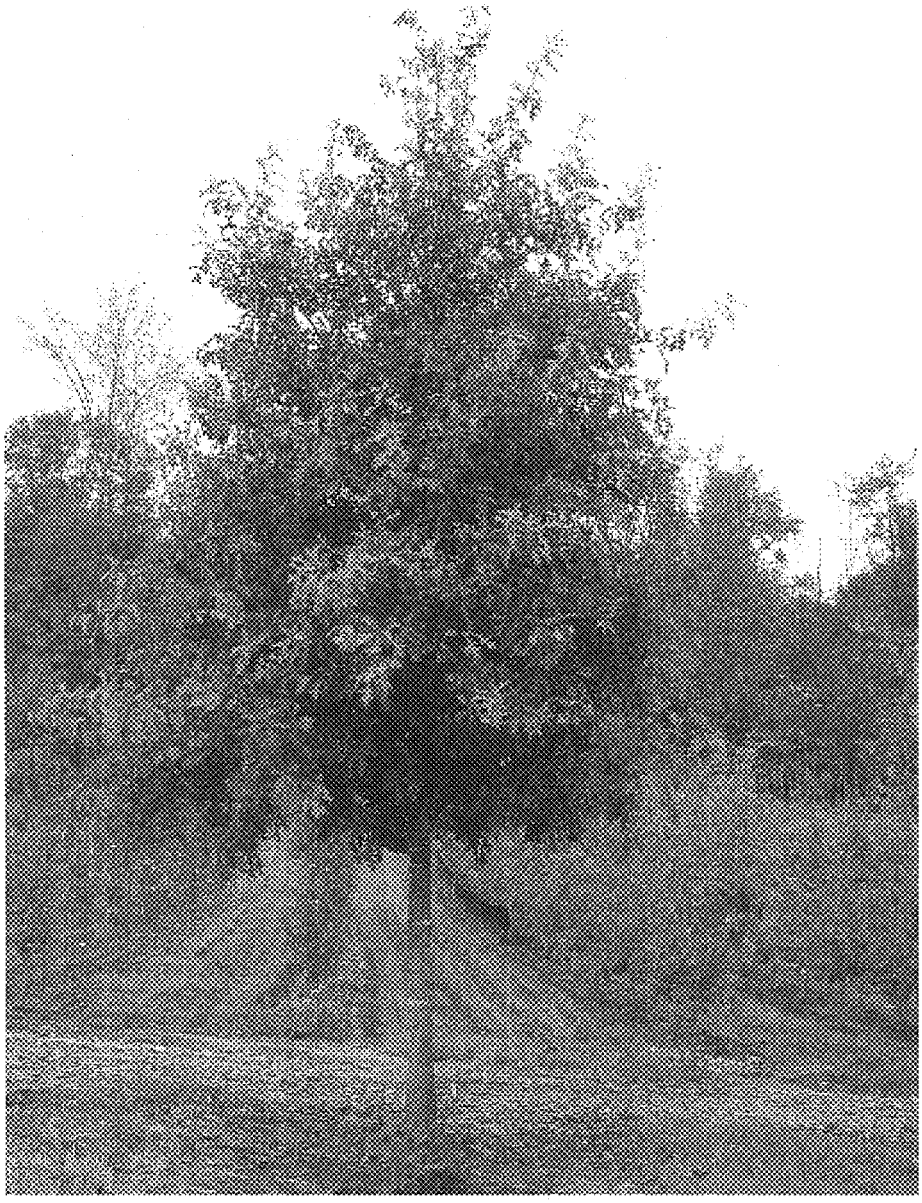
FIG. 2 is a photograph of the original tree of my new variety in summer leaf.

Tree shape: The original tree has a dense canopy, with a central leader (FIGS. 1 and 2).

Size and growth rate: The original tree is currently 5.5 inches in caliper at 12 inches above the ground, about 20 feet high, and about 11 feet wide, thus providing an overall height to width ratio of about 1.8. Prior to transplanting to the observation site, the original tree had an average growth in caliper of about 0.92 inches per year. Root development from time of sticking is approximately six to eight weeks.

Figure 7:
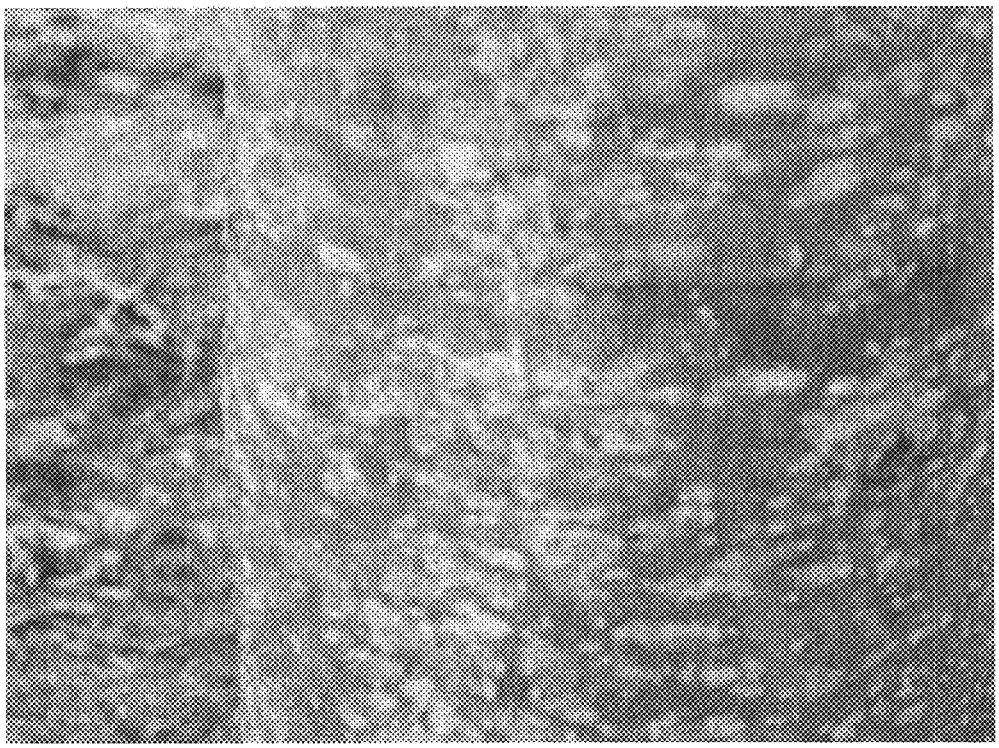
FIG. 7 is a close up of a typical section of the trunk of the original tree of the new variety.

Trunk: Bark is typical of the species (FIG. 7), being smooth and gray (grayed-green) (RHS 188B) with patches of light gray (RHS 156D) on young trees, with age, becoming roughened by shallow ridges and furrows. Mature bark is darker gray (RHS 198B) with patches of light gray (RHS 156D), also typical of the species.

Branching habit: Primary branches emerge from the trunk at about a 65 degree angle to the leader. Some of the branches in the top one-half of the tree emerge at slightly less of an angle, approx. 50 degree angle to the leader. We expect with age the angle to increase with respect to the leader.

Figure 3:
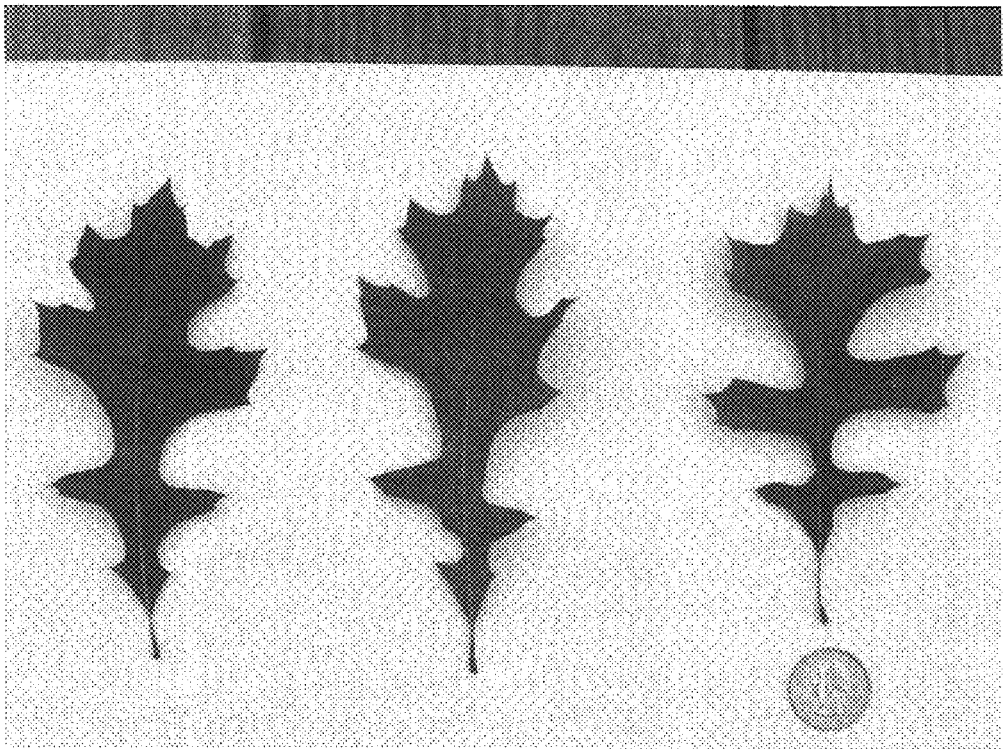
FIG. 3 is a close up of three single leaves depicting the upper side of leaves from of tree of my new variety. The U.S. Quarter Dollar in the picture provides a sizing reference.
Figure 4:
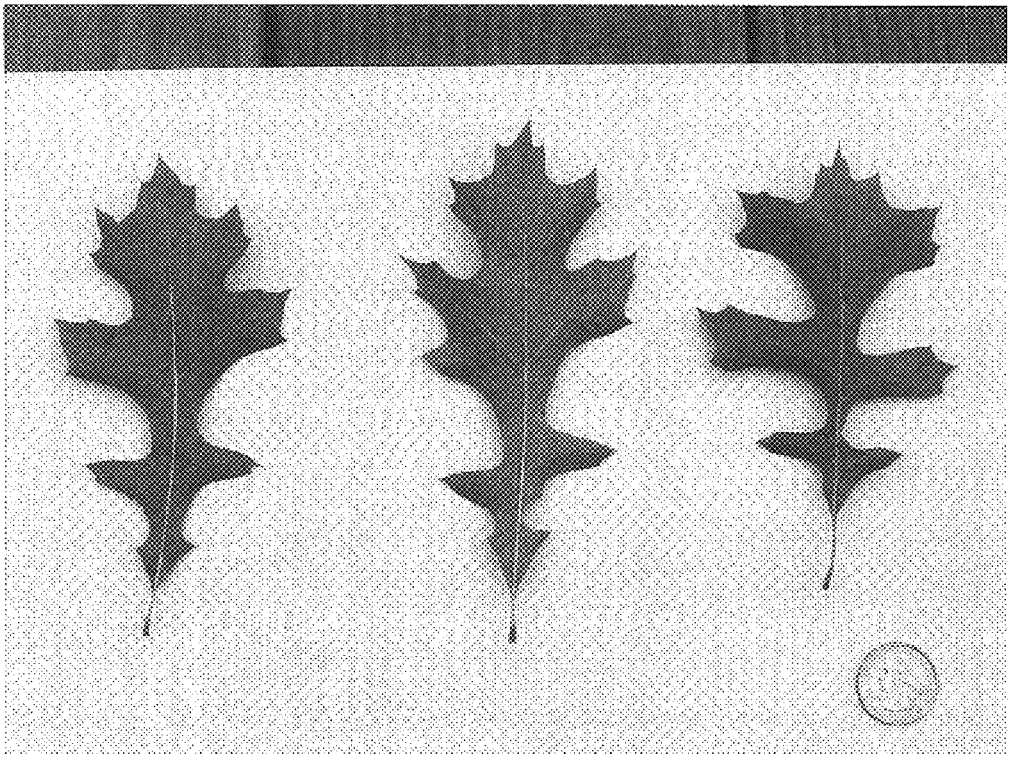
FIG. 4 is a close up of three single leaves depicting the under side of leaves from a tree of my new variety.
Figure 5:
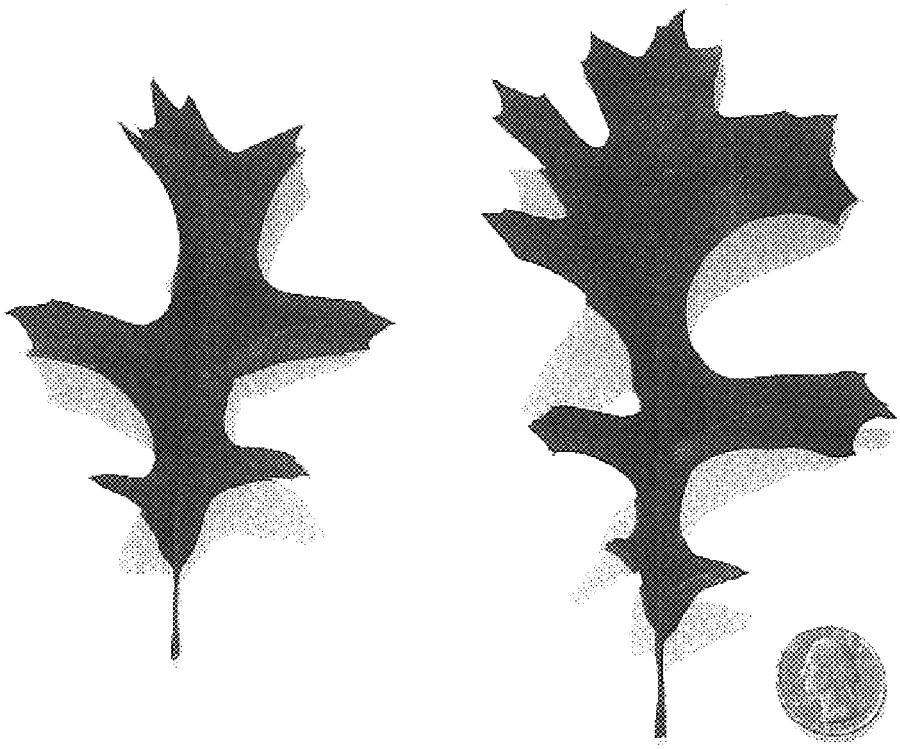
FIG. 5 is a close up of two leaves depicting the new growth color during the spring.
Figure 6:
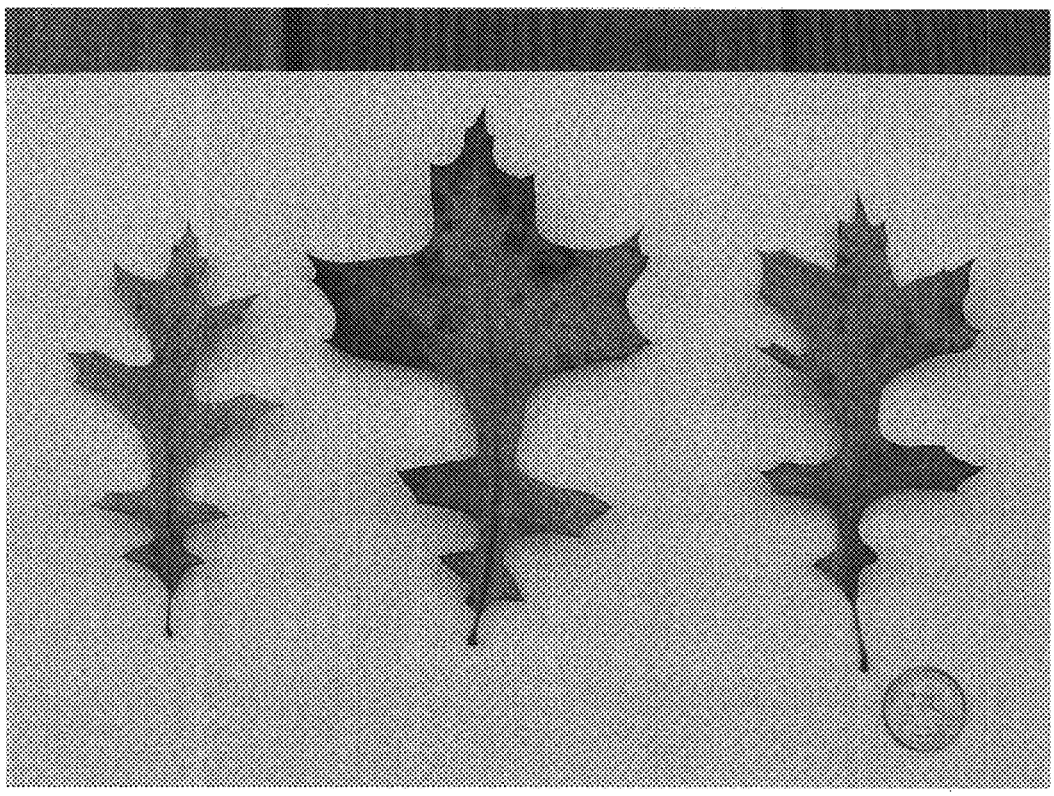
FIG. 6 is a close up of three leaves depicting fall leaf color of my new variety.

Foliage: The leaves of Nuttall, Shumard, and Pin all resemble one another, and my tree has leaves that are typical of the species *Q. nuttallii* in size and shape: Alternate, simple, obovate to elliptic, 4 to 9" long, 2 to 5" wide, with 5 to 9 lobes. Sinuses are round with narrow lobes. The leaves maintain a dark green upper surface color in summer (FIG. 3) (RHS 137C), and the lower leaf surface (FIG. 4) is a lighter green (RHS 138B). My new tree has consistent fall color (FIG. 6) which ranges from orange-red (RHS 32B) to yellow-orange (RHS 17D). New growth in the spring (FIGS. 1 and 5) is a consistent deep red (RHS 59A) and persists into summer. The stems turn a deep red (RHS 59A) in the spring during leaf out before turning back to their summer color.

Petiole: Average length is between ⅝" and ⅞". The color of the petiole on summer foliage is a yellow green (RHS 145B). The petiole on new growth is red (RHS 42A).

Buds: Typical of the species, being imbricate, ⅛ to ¼" long, ash-gray (RHS 197C) to brown-gray (RHS 199B), and pubescent with ciliate scale margins.

Flowers: Typical of the species. However, most oaks have flowers so similar that it is difficult to distinguish between species based on flower type alone. The trees are monoecious. The staminate catkins are pendent and clustered. The individual flowers comprise a 4- to 7-lobed calyx that encloses 6 to 12 stamens. Pistillate flowers are solitary or in few to many-flowered spikes from the axils of the new leaves. Individual pistillate flowers consist of a 6-lobed calyx surrounding the ovary, with the whole party enclosed in an involucre.

Fruit: Acorns have only been observed in the original tree of my variety and are typical of the Nuttall Oak species. Acorns are ovate, ¾ to 1¼" long, short-stalked, oblong-ovoid, and covered ⅓ to ½ by the cap. The acorn is gray-orange (RHS 165A) with dark brown (RHS 200B) striations. The cap is light brown (RHS 199C).

Root system: The root system is typical of the species being fibrous.

Winter hardiness: Observed to be hardy in at least USDA Hardiness Zone 7. My new tree variety has not been observed under multiple Zones.

Disease and pest resistance: My new tree variety appears to be typical of the species.

I claim:

1. A new and distinct variety of oak tree substantially as herein shown and described, characterized by its dense branching habit and its consistent red new growth persisting in summer.

* * * * *

UNITED STATES PATENT AND TRADEMARK OFFICE

CERTIFICATE OF CORRECTION

PATENT NO. : PP 16,254 P3
APPLICATION NO. : 10/850689
DATED : February 14, 2006
INVENTOR(S) : Michael M. Glenn It is certified that error appears in the above-identified patent and that said Letters Patent is hereby corrected as shown below:

Column 1,
Line 31, "Texas Road Oak" should be -- Texas Red Oak --.

Column 5,
Line 3, "party" should be -- partly --.

Signed and Sealed this

Twenty-seventh Day of June, 2006

JON W. DUDAS
*Director of the United States Patent and Trademark Office*